United States Patent
Dziech et al.

(10) Patent No.: US 6,608,478 B1
(45) Date of Patent: Aug. 19, 2003

(54) ROTOR SLOT BOTTOM INSPECTION APPARATUS AND METHOD

(75) Inventors: Michael Leonard Dziech, Cincinnati, OH (US); Joseph Anthony Traxler, Hamilton, OH (US); Michael Wayne Fields, Loveland, OH (US)

(73) Assignee: General Electric Company, Schenectady, NY (US)

( * ) Notice: Subject to any disclaimer, the term of this patent is extended or adjusted under 35 U.S.C. 154(b) by 2 days.

(21) Appl. No.: 10/011,190

(22) Filed: Dec. 7, 2001

(51) Int. Cl.[7] ........................ G01N 27/90; G01N 33/12
(52) U.S. Cl. .................... 324/262; 324/219; 324/238; 73/866.5
(58) Field of Search ................................ 324/219, 228, 324/238–242, 260–262; 33/542–544.1; 73/618–625, 661, 866.5

(56) References Cited

U.S. PATENT DOCUMENTS

| | | | |
|---|---|---|---|
| 4,457,176 A | * | 7/1984 | Scholz ........................ 73/624 |
| 4,644,274 A | * | 2/1987 | Casarcia ..................... 324/262 |
| 5,065,635 A | * | 11/1991 | Burtner et al. ............. 73/866.5 |
| 5,315,234 A | * | 5/1994 | Sutton et al. ................ 324/242 |
| 5,345,514 A | | 9/1994 | Mahdavieh et al. ........ 382/152 |
| 5,442,286 A | | 8/1995 | Sutton, Jr. et al. .......... 342/242 |
| 5,479,834 A | | 1/1996 | Sanagawa et al. .......... 73/866.5 |
| 5,781,007 A | | 7/1998 | Partika et al. ............... 324/220 |
| 5,903,147 A | * | 5/1999 | Granger et al. ............. 324/219 |
| 6,114,849 A | * | 9/2000 | Price et al. .................. 324/240 |
| 6,198,280 B1 | * | 3/2001 | Hensley et al. ............. 324/237 |
| 6,250,166 B1 | * | 6/2001 | Dingwell et al. ............ 73/810 |

* cited by examiner

*Primary Examiner*—Edward Lefkowitz
*Assistant Examiner*—Darrell Kinder
(74) *Attorney, Agent, or Firm*—V. Ramaswamy; Gregory O. Garmong

(57) ABSTRACT

A rotor disk is inspected using an inspection apparatus including an inspection fixture which has a base, and at least one guide extending from the base. Each guide is slidably engagable to one of the rotor slots of the rotor disk and has a guide side shaped to slidably conform to the rotor slot side, and a guide bottom having a guide bottom surface which, in combination with a slot bottom surface, defines an elongated inspection cavity extending parallel to the axis of revolution of the rotor disk. The inspection fixture is mated to the rotor disk such that each guide slides into one of the rotor slots. A sensor apparatus includes a sensor, such as an eddy current sensor, sized to slide into the inspection cavity with a close facing relation thereto, and a sensor drive that moves the sensor parallel to a direction of elongation of the inspection cavity. Inspection is performed by inserting the sensor into the inspection cavity, and sensing the rotor slot bottom using the sensor.

19 Claims, 5 Drawing Sheets

ROTOR SLOT BOTTOM INSPECTION APPARATUS AND METHOD

This invention relates to the inspection of rotor slot bottoms of rotor disks and, more particularly, to a fixture that aids in performing the inspections.

BACKGROUND OF THE INVENTION

In an aircraft gas turbine (jet) engine, air is drawn into the front of the engine, compressed by a shaft-mounted compressor, and mixed with fuel. The mixture is combusted, and the resulting hot combustion gases are passed through a turbine mounted on the same shaft. The flow of gas turns the turbine by contacting an airfoil portion of the turbine blade, which turns the shaft and provides power to the compressor. The hot exhaust gases flow from the back of the engine, driving it and the aircraft forward. There may additionally be a turbofan that drives a bypass flow of air rearwardly to improve the thrust of the engine.

The compressor, the turbine, and the turbofan have a similar construction, in that they each include a rotor disk and a set of removable blades extending radially outwardly from the rotor disk. The rotor disk has a series of rotor slots extending parallel to the axis of revolution of the rotor disk, and the roots of the blades are slidably engaged into the slots. The slots and the roots of the blades are conformably shaped to hold the blades in the rotor disk when the rotor disk rotates about its axis of rotation. In current practice, the rotor slots and the roots of the blades have a conformable dovetail shape. While the compressor, the turbine, and the turbofan share this basic configuration, the materials of construction of the rotor disks and the blades, as well as the shapes and sizes of the rotor disks and the blades, vary in these different sections of the gas turbine engine.

One of the failure modes of the rotor disk is the formation of cracks in the bottoms of the rotor slots. These cracks typically initiate due to a combination of creep and fatigue. One of the cracks eventually may enlarge sufficiently that it propagates and leads to a catastrophic failure of the rotor disk.

To avoid such a failure, the slot bottoms are periodically inspected using visual or fluorescent penetrant inspection (FPI) techniques. These techniques identify cracks at the bottoms of the slots when they are small and before they can grow to a size that they propagate, so that the cracks may be repaired. These techniques, while operable, are subjective in that they depend upon the skill, judgment, and state of mind of the person performing the inspection. They are only semiquantitative in nature, in that the number, length, and type of cracks are subjectively judged. Visual and FPI approaches are also not always reproducible and do not lend themselves to automation of the inspection.

There is accordingly a need for an approach which improves upon the existing inspection techniques. The present invention fulfills this need, and further provides related advantages.

SUMMARY OF THE INVENTION

The present invention provides an inspection apparatus and method for inspecting the slot bottoms of rotor slots. The present approach provides for objective analysis of the state of the slot bottoms. It does not depend upon the state of mind of the person performing the test, yields quantitative results, provides for extensive automation of the inspection procedure, and has excellent reproducibility of the inspection.

An inspection apparatus is used in relation to a rotor disk having a plurality of circumferentially adjacent rotor slots therein extending parallel to an axis of revolution of the rotor disk. Each rotor slot has a rotor slot side and a rotor slot bottom with a slot bottom surface. The inspection apparatus comprises an inspection fixture including a base, and at least one guide extending from the base. Each guide is slidably engagable to one of the rotor slots and has a guide side shaped to slidably conform to the rotor slot side. Each guide further has a guide bottom with a guide bottom surface which, in combination with the slot bottom surface, defines an elongated inspection cavity, which is preferably substantially cylindrical with its cylindrical axis extending parallel to the axis of revolution of the rotor disk. Preferably, the inspection fixture comprises more than one guide, each guide as set forth above. The guides are spaced apart and angled so as to slidably engage the respective rotor slots of the rotor disk.

The inspection apparatus may further include a sensor apparatus comprising a sensor sized to slide into the inspection cavity. The sensor is preferably an eddy current sensor. The sensor apparatus typically also includes a sensor drive that moves the sensor parallel to a direction of elongation of the inspection cavity. In the case of the eddy current sensor, the sensor drive rotates the sensor about its sensor axis while in the inspection cavity. Eddy current inspection of the slot bottoms is an important advance over visual and FPI techniques. It may be automated and is not dependent upon operator skill. It produces quantitative results that are reproducible. In the preliminary development by the inventors leading to the present invention, the advantages of eddy current inspection were recognized but could not be achieved because the sensor could not be positioned sufficiently accurately relative to the slot bottoms. The inspection fixture solves this problem, allowing the eddy current sensor to be precisely and reproducibly positioned relative to the slot bottoms during the inspection procedure, so that its full advantages may be achieved.

The inspection apparatus is used to inspect a rotor disk as described above. The method includes providing an inspection apparatus comprising the inspection fixture as described above, and assembling the inspection fixture to the rotor disk such that each guide slides into one of the rotor slots. The sensor apparatus as described above is provided, and the sensor is inserted into the inspection cavity. The rotor slot bottom is sensed using the sensor. Preferably, the sensor drive rotates the eddy current sensor about its sensor axis and also permits moving the eddy current sensor parallel to the direction of elongation of the inspection cavity during the sensing operation.

The inspection fixture precisely positions the sensor of the sensor apparatus. The sensor must be tightly constrained to a close facing contact to the slot bottom surface during the inspection process. If the sensor were allowed to separate from the surface of the slot bottom by even 0.001 inch, the inspection sensitivity would be reduced and defects might be undetected. The inspection fixture, sensor drive, and split-sensor structure cooperate to ensure that the sensor remains in intimate contact with the slot bottom. In the preferred case where the sensor is an eddy current sensor, the intimate contact is maintained as the sensor is rotated about its sensor axis and moved parallel to the sensor axis.

Although a particular embodiment of the invention has been described in detail for purposes of illustration, various modifications and enhancements may be made without departing from the spirit and scope of the invention. Accordingly, the invention is not to be limited except as by the appended claims.

DETAILED DESCRIPTION OF THE INVENTION

Figure 1:
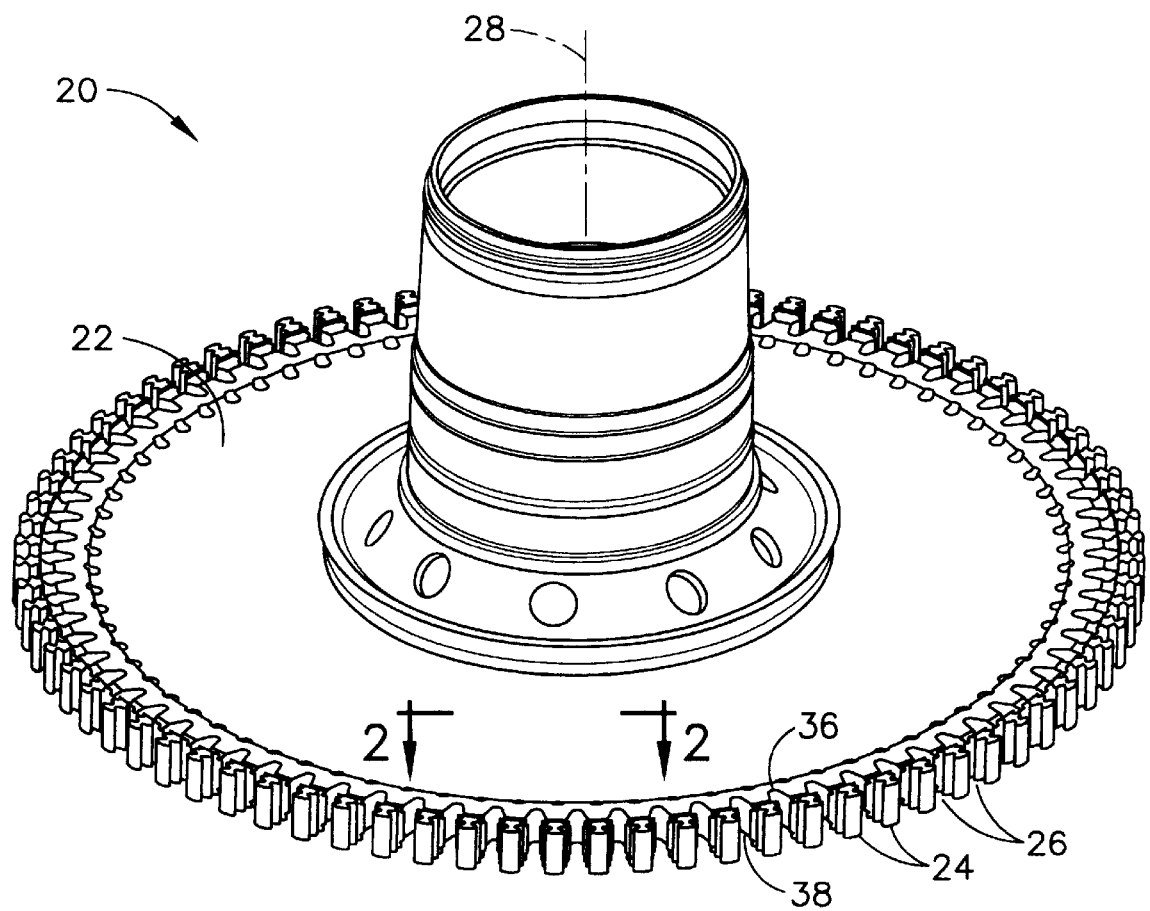
FIG. 1 is a perspective view of a rotor disk.
Figure 2:
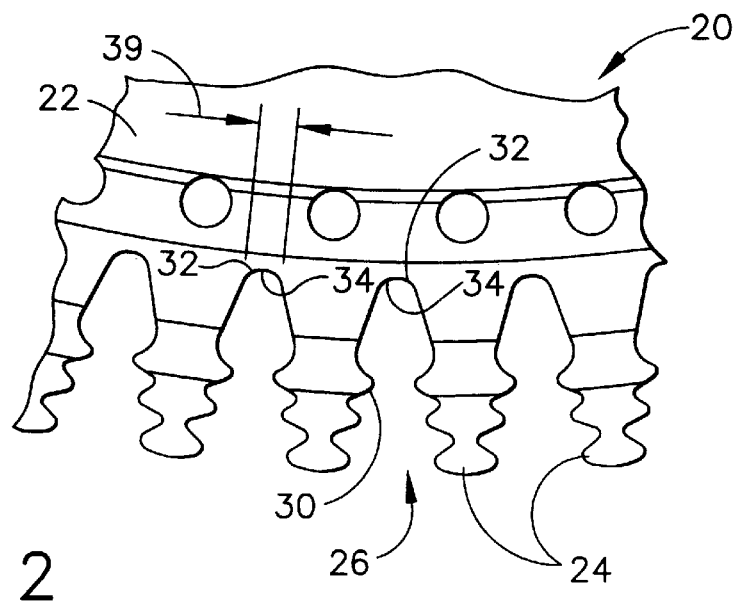
FIG. 2 is a detail sectional view of the rotor disk of FIG. 1, taken along line 2—2.
Figure 3:
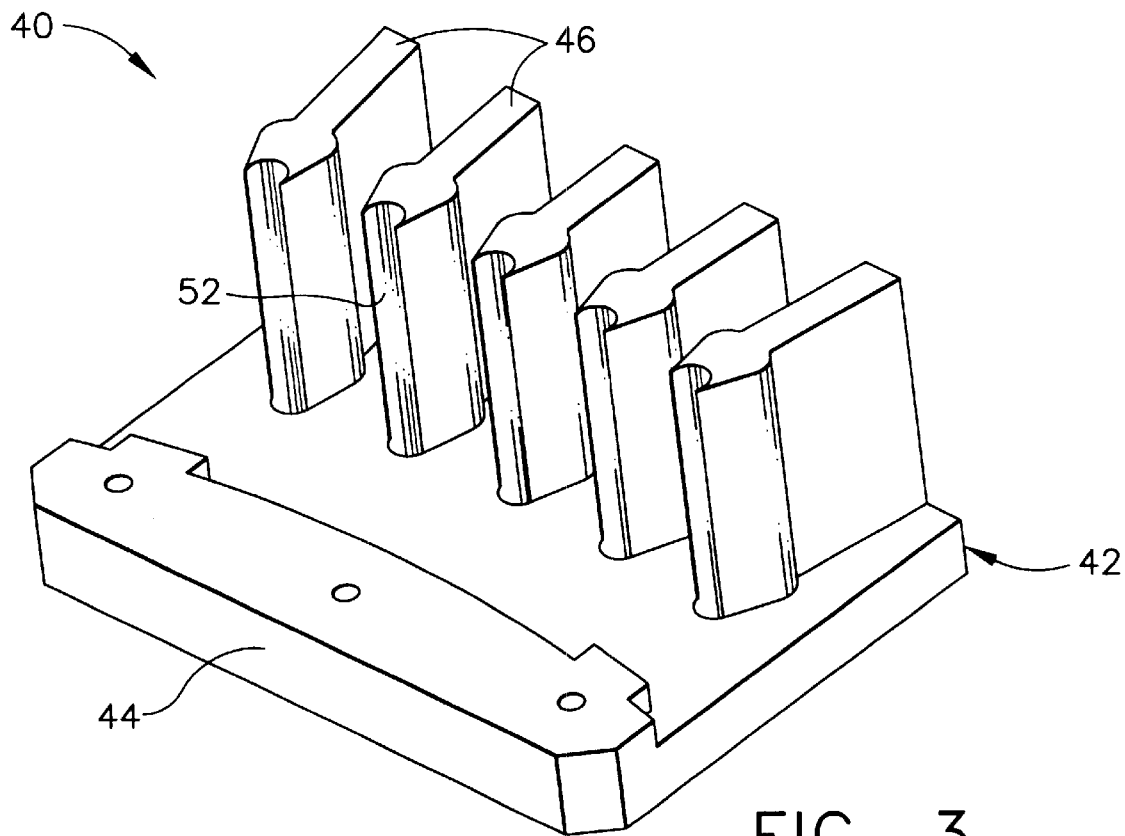
FIG. 3 is a perspective view of the inspection fixture from a bottom side.

FIGS. 1–2 depict a rotor disk 20 from a gas turbine engine. The rotor disk 20 may be a turbine disk, a compressor disk, or a fan disk. The rotor disk 20 includes a web 22 and a plurality of circumferentially adjacent dovetail posts 24 that extend radially outwardly from the web 22. There are a plurality of rotor slots 26, one between each pair of the dovetail posts 24. The rotor slots 26 extend parallel to an axis of revolution 28 of the rotor disk 20, which is parallel to the axis of the gas turbine engine. Each rotor slot 26 has a forward end 36 and an aft end 38, relative to the axis of revolution 28. Each rotor slot 26 has a rotor slot side 30, whose shape is defined by the shape of the dovetail posts 24, and a rotor slot bottom 32 with a concave slot bottom surface 34. It is desired to inspect the rotor slot bottoms 32 over an inspection arc whose subtended distance is indicated by the dimension 39 in FIG. 2.

An inspection apparatus 40 used to inspect the rotor slot bottoms 32 of the rotor disk 20 includes an inspection fixture 42 illustrated in FIGS. 3–6. The inspection fixture 42 includes a base 44 and at least one guide 46 extending from the base 44. Each guide 46 has a guide side 48 shaped to slidably conform to the rotor slot side 30. That is, each guide 46 is shaped so that it is received into and slides into (sliding parallel to the axis of revolution 28) one of the rotor slots 26 between two adjacent dovetail posts 24, with the guide side 48 in facing relation to the rotor slot slide 30. In the illustrated embodiment, there are five guides 46. As may be seen in FIG. 6, the guides 46 are angled from the base 44 and spaced apart so as to slidably engage respective rotor slots 26 of the rotor disk 20. Each guide 46 is shaped and sized to be slidably engagable to one of the rotor slots 26.

Figure 6:
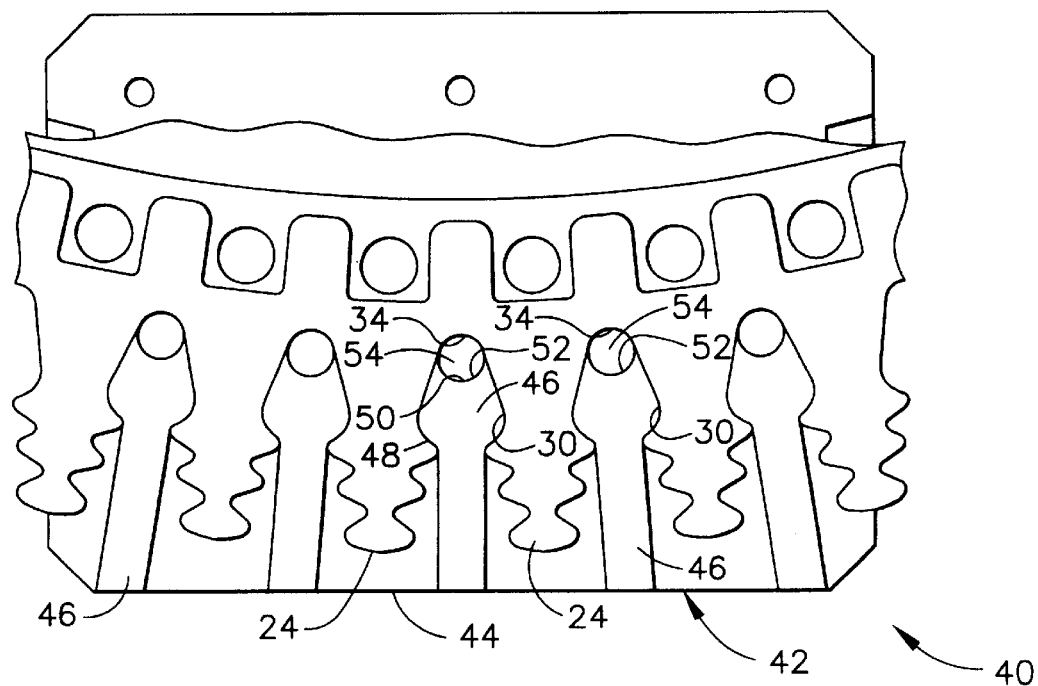
FIG. 6 is a sectional view like that of FIG. 2, with the inspection fixture installed.

As best seen in FIG. 6, each guide 46 has a guide bottom 50 with a concave guide bottom surface 52. In combination with the concave slot bottom surface 34, the guide bottom surface 52 defines an elongated inspection cavity 54 extending parallel to the axis of revolution 28 of the rotor disk 20 (i.e., out of the plane of the page in FIG. 6). The inspection cavity 54 is preferably substantially cylindrical, with a cylindrical axis extending parallel to the axis of revolution 28. The inspection cavity 54 need not be a perfect cylinder, but the guide bottom surface 52 and the slot bottom surface 34, taken together, approximately define a cylindrical surface. Each inspection cavity 54 extends the entire length of the dovetail post 24, measured parallel to the axis of revolution 28.

Figure 7:
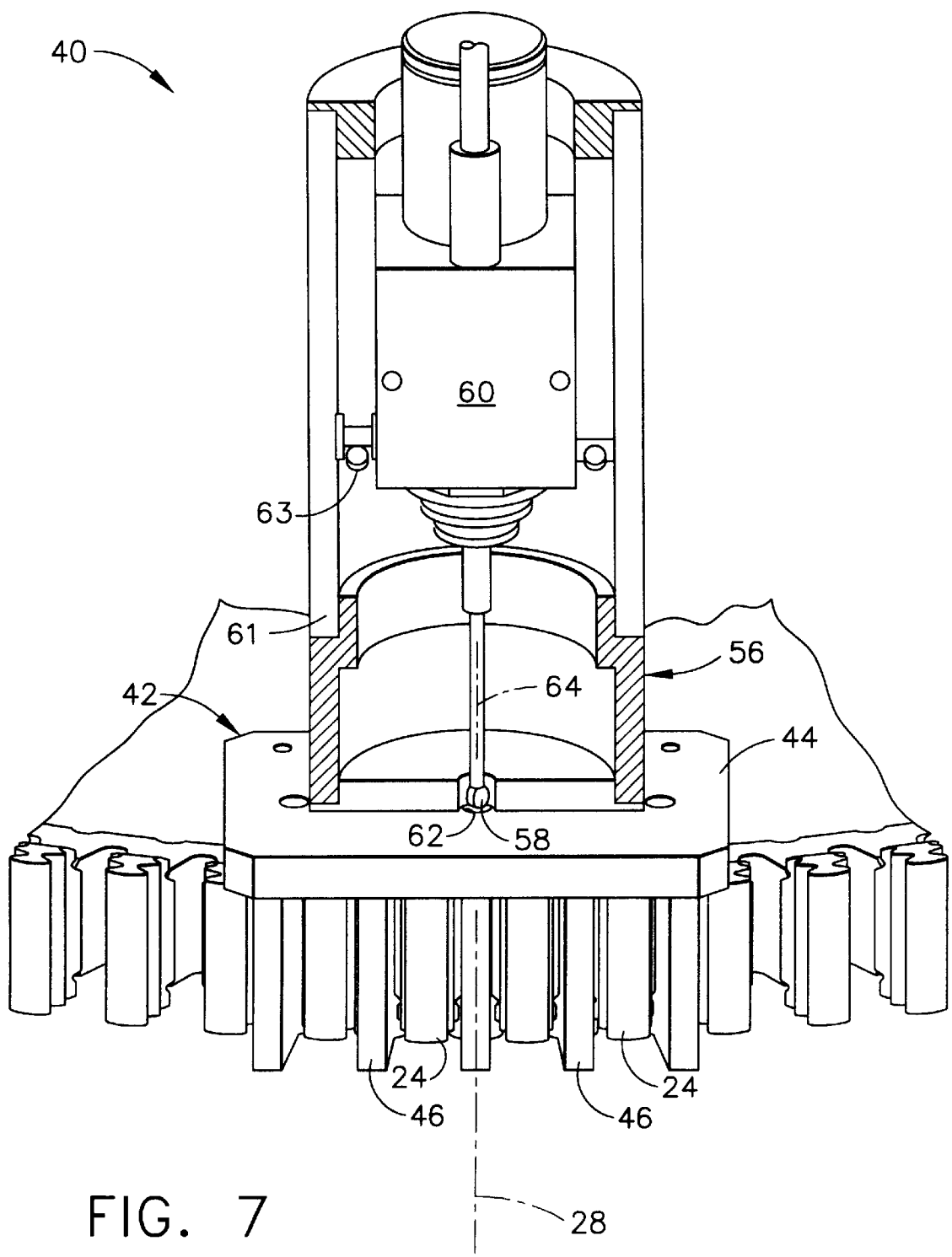
FIG. 7 is a perspective view of a portion of the rotor disk, with the inspection fixture installed and the sensor apparatus in position to begin an inspection of a slot bottom.

As shown in FIG. 7, the inspection apparatus 40 also includes a sensor apparatus 56 comprising a sensor 58 sized to slide into the inspection cavity 54 with a light slip fit. The sensor 58 may be of any operable type, but is preferably an eddy current sensor that is pressed against the slot bottom surface 34 to measure the eddy current response in the rotor slot bottom 32 of the rotor disk 20. The eddy current sensor 58 is in the form of a split ball which is spring loaded and sprung outwardly so that the sides of the ball contact the sides of the inspection cavity 54 when the sensor 58 is inserted into the inspection cavity 54. In the case of the eddy current inspection apparatus, a sensor drive 60 is mounted to a sensor guide support 61 on a linear drive 63 that allows the sensor drive 60 to be moved parallel to the axis of revolution 28. The sensor drive 60 rotates the sensor 58 about a sensor axis 64 that is parallel to the axis of revolution 28 of the sensor disk 20, typically at about 1000–3000 revolutions per minute. The sensor drive 60 also allows the sensor 58 to be moved parallel to the direction of elongation of the inspection cavity 54 (i.e., parallel to the axis of revolution 28) using the linear drive 63. In the preferred case, the rotational movement of the sensor drive 60 is powered by an electric motor, and the linear drive parallel to the axis of revolution is achieved manually on the linear drive 63.

Figure 4:
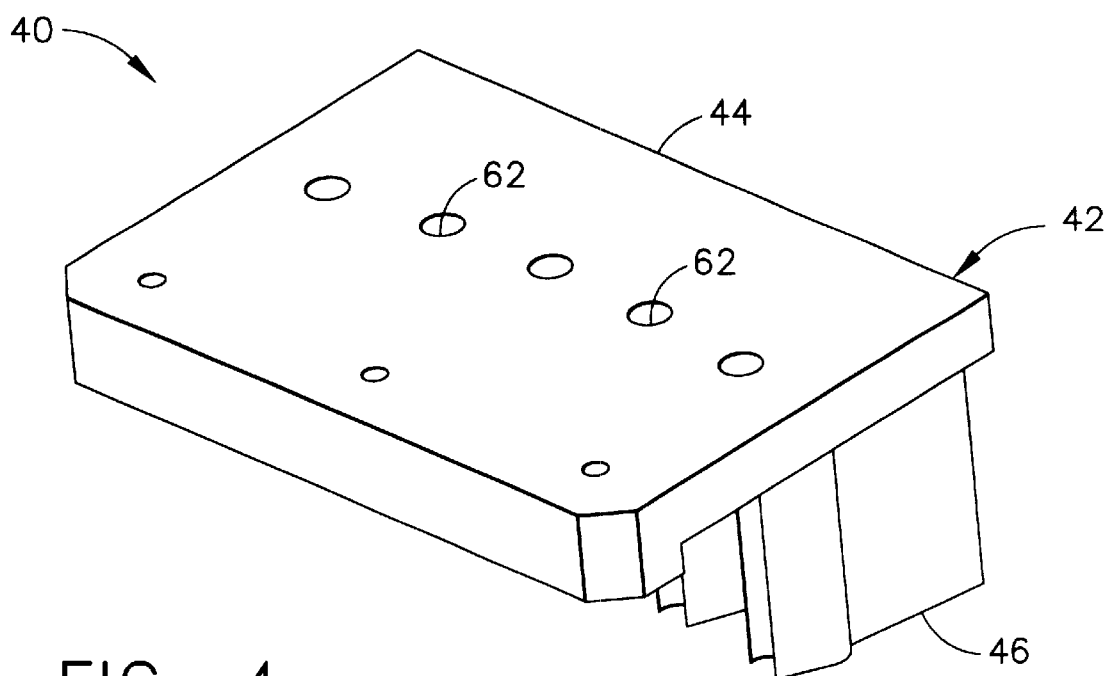
FIG. 4 is a perspective view of the inspection fixture from a top side.
Figure 5:
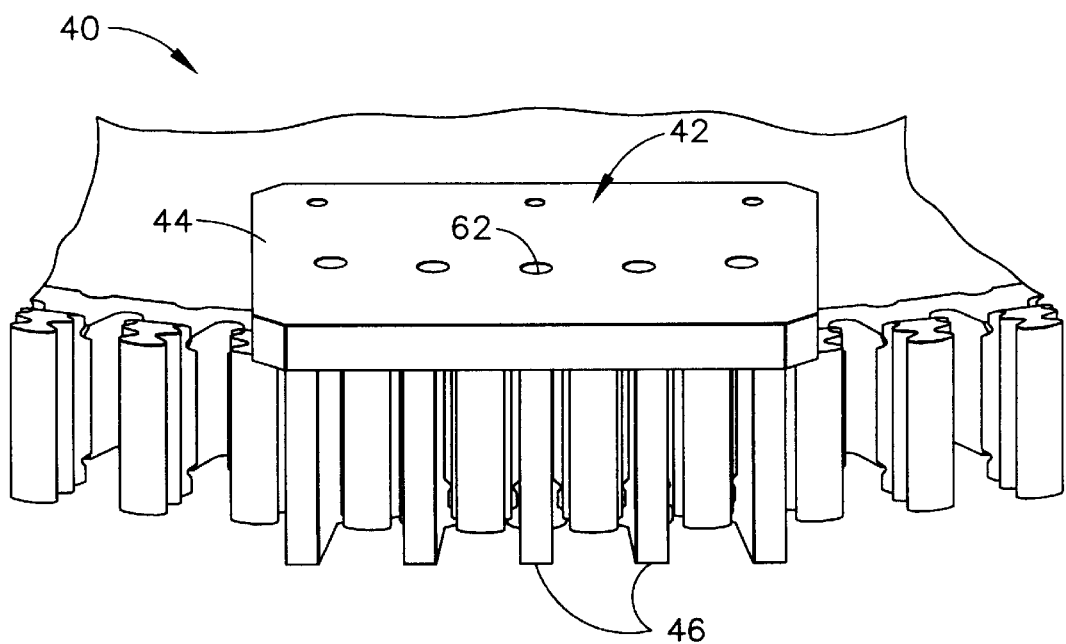
FIG. 5 is a perspective view of a portion of the rotor disk with the inspection fixture installed thereto.

The sensor 58 gains access to the inspection cavity 54 through inspection ports 62 in the base 44 of the inspection fixture 42, which are visible in FIGS. 4–6 and which align with the respective inspection cavities 54. As the sensor 58 is pushed into the inspection cavity 54, the split ball is compressed slightly to achieve a light slip fit between the sensor 58 and the walls of the inspection cavity 54. The sensor 58 thus has a close facing relation to the slot bottom surface 34. Alternatively, the inspection fixture 42 may be inverted so that the sensor 58 is inserted into an end of each inspection cavity that is remote from the base 44. The sensor drive 60 slides the sensor 58 along the inspection cavity 54 with the sensor 58 in facing relation to the slot bottom surface 34. A sensor output signal is transmitted through a cable 66 to an external electronic instrumentation (not shown) used in its analysis.

The inspection fixture 42 provides the guide bottom surface 52. The guide bottom surface 52 and the slot bottom surface 34 together define the shape of the inspection cavity 54. The sensor 58 is sized to be slidably received within the inspection cavity 54 with the light slip fit as the split ball of the sensor 58 is compressed, so that the sensor 58 is held in close proximity to the slot bottom surface 34. The sensor 58 is thereby able to make precise and reproducible measurements of the rotor slot bottom 32 of the rotor disk 20.

Figure 8:
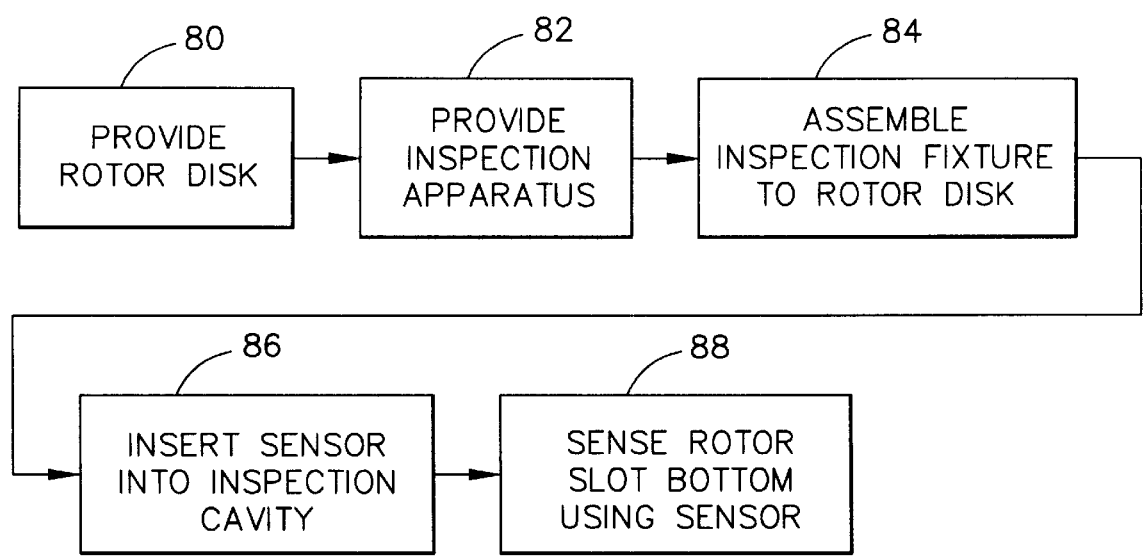
FIG. 8 is a block flow diagram of an approach for performing an inspection of the slot bottom.

FIG. 8 depicts an approach for practicing the invention. The rotor disk 20 as described above is provided, numeral 80. The inspection apparatus 40 as described above is provided, numeral 82. The inspection fixture 42 is assembled to the rotor disk 20 such that each guide 46 slides into one of the rotor slots 26 as described above, numeral 84. The sensor apparatus 56 is assembled to the inspection fixture 42 and the rotor disk 20 as in FIG. 7. The sensor 58 is inserted into the inspection cavity 54, numeral 86, and the rotor slot bottom 32 is sensed using the sensor 58, numeral 88. After the first rotor slot bottom 32 is sensed and inspected, the sensor 58 is withdrawn from the inspection cavity 54, the sensor apparatus 56 is indexed to align the sensor 58 with the next inspection cavity 54, and steps 86 and 88 are repeated. After all of the rotor slot bottoms 32 corresponding to one positioning of the inspection fixture 42 have been inspected, the inspection fixture 42 is withdrawn, moved to a new location, and steps 84, 86, and 88 are repeated as necessary. This procedure is repeated until all of the rotor slot bottoms 32 of the rotor disk 20 have been inspected.

A suitable sensor drive 60 may be obtained commercially from vendors such as Rohman, Inc., Frankenthal, Germany, and Staveley, Inc., Kenewick, Wash. The inspection fixture 42, the sensor 58, and the sensor guide support 61 were built by the inventors.

The approach of the invention has been reduced to practice using the apparatus of FIG. 7 and the method of FIG. 8. The present approach is highly repeatable and sensitive to the presence of defects in the rotor slot bottom. It is also not dependent upon operator skill and mental state. Alternative inspection procedures such as magnified visual and fluorescent penetrant inspection are highly subjective and vary among individual inspectors. The present approach provides quantitative information that may be judged by objective criteria.

Although a particular embodiment of the invention has been described in detail for purposes of illustration, various modifications and enhancements may be made without departing from the spirit and scope of the invention. Accordingly, the invention is not to be limited except as by the appended claims.

What is claimed is:

1. An inspection apparatus used in relation to a rotor disk having a plurality of circumferentially adjacent rotor slots therein extending parallel to an axis of revolution of the rotor disk, each rotor slot having a rotor slot side and a rotor slot bottom with a slot bottom surface, the inspection apparatus comprising an inspection fixture including:
   a base; and
   at least one guide extending from the base, each guide being slidably engagable to one of the rotor slots and having
      a guide side shaped to slidably conform to the rotor slot side, and
      a guide bottom having a guide bottom surface which, in combination with the slot bottom surface, defines an elongated inspection cavity extending parallel to the axis of revolution of the rotor disk.

2. The inspection apparatus of claim 1, wherein the inspection fixture comprises more than one guide, each guide as set forth in claim 1, with the guides being spaced apart and angled so as to slidably engage respective rotor slots of the rotor disk.

3. The inspection apparatus of claim 1, wherein the inspection cavity is substantially cylindrical.

4. The inspection apparatus of claim 1, further including a sensor apparatus comprising
   a sensor sized to slide into the inspection cavity.

5. The inspection apparatus of claim 1, further including a sensor apparatus comprising
   a sensor sized to slide into the inspection cavity, and
   a sensor drive that moves the sensor parallel to a direction of elongation of the inspection cavity.

6. The inspection apparatus of claim 1, further including a sensor apparatus comprising
   an eddy current sensor sized to slide into the inspection cavity with a close facing relation thereto.

7. The inspection apparatus of claim 1, further including a sensor apparatus comprising
   an eddy current sensor sized to slide into the inspection cavity with a close facing relation thereto, and
   a sensor drive that rotates the eddy current sensor about a direction of elongation of the inspection cavity and moves the eddy current sensor parallel to the direction of elongation of the inspection cavity.

8. An inspection apparatus used in relation to a rotor disk having a plurality of circumferentially adjacent rotor slots therein extending parallel to an axis of revolution of the rotor disk, each rotor slot having a rotor slot side and a rotor slot bottom with a slot bottom surface, the inspection apparatus comprising an inspection fixture including:
   a base; and
   a plurality of guides extending from the base, each guide being slidably engagable to a respective one of the rotor slots and having
      a guide side shaped to slidably conform to the rotor slot side, and
      a guide bottom having a guide bottom surface which, in combination with the slot bottom surface, defines an substantially cylindrical inspection cavity having a cavity axis extending parallel to the axis of revolution of the rotor disk.

9. The inspection apparatus of claim 8, further including a sensor apparatus comprising
   a sensor sized to slide into the inspection cavity.

10. The inspection apparatus of claim 8, further including a sensor apparatus comprising
    a sensor sized to slide into the inspection cavity, and
    a sensor drive that moves the sensor parallel to a direction of elongation of the inspection cavity.

11. The inspection apparatus of claim 8, further including a sensor apparatus comprising
    an eddy current sensor sized to slide into the inspection cavity with a close facing relation thereto.

12. The inspection apparatus of claim 8, further including a sensor apparatus comprising
    an eddy current sensor sized to slide into the inspection cavity with a close facing relation thereto, and
    a sensor drive that rotates the eddy current sensor about a direction of elongation of the inspection cavity and moves the eddy current sensor parallel to the direction of elongation of the inspection cavity.

13. A method of inspecting a rotor disk, comprising the steps of
    providing a rotor disk having a plurality of circumferentially adjacent rotor slots therein extending parallel to an axis of revolution of the rotor disk, each rotor slot having a rotor slot side and a rotor slot bottom with a slot bottom surface;
    providing an inspection apparatus comprising an inspection fixture, the inspection fixture including
       a base, and
       at least one guide extending from the base, each guide being slidably engagable to one of the rotor slots and having
          a guide side shaped to slidably conform to the rotor slot side, and
          a guide bottom having a guide bottom surface which, in combination with the slot bottom surface, defines an elongated inspection cavity extending parallel to the axis of revolution of the rotor disk; and
    assembling the inspection fixture to the rotor disk such that each guide slides into one of the rotor slots.

14. The method of claim 13, wherein the step of providing the inspection apparatus includes the step of
    providing the inspection fixture with more than one guide, each guide as set forth in claim 13, with the guides being spaced apart and angled so as to slidably engage respective rotor slots of the rotor disk.

15. The method of claim 13, wherein the step of providing the inspection apparatus includes the steps of
providing the inspection fixture having the guide bottom surface such that the inspection cavity is substantially cylindrical.

16. The method of claim 13, wherein the step of providing the inspection apparatus includes the additional step of
providing a sensor apparatus comprising a sensor sized to slide into the inspection cavity.

17. The method of claim 13, wherein the step of providing the inspection apparatus includes the additional step of
providing a sensor apparatus comprising
a sensor sized to slide into the inspection cavity, and
a sensor drive that moves the sensor parallel to a direction of elongation of the inspection cavity, and wherein the method includes an additional steps of
inserting the sensor into the inspection cavity, and
sensing the rotor slot bottom using the sensor.

18. The method of claim 13, wherein the step of providing the inspection apparatus includes the additional step of
providing a sensor apparatus comprising an eddy current sensor sized to slide into the inspection cavity with a close facing relation thereto and rotate within the inspection cavity.

19. The method of claim 13, wherein the step of providing the inspection apparatus includes the additional step of
providing a sensor apparatus comprising
an eddy current sensor sized to slide into the inspection cavity with a close facing relation thereto, and
a sensor drive that moves the eddy current sensor parallel to a direction of elongation of the inspection cavity, and wherein the method includes additional steps of
inserting the eddy current sensor into the inspection cavity, and
sensing the rotor slot bottom using the eddy current sensor.

* * * * *